(12) United States Patent
Stockel

(10) Patent No.: US 7,074,459 B2
(45) Date of Patent: Jul. 11, 2006

(54) METHOD FOR PRESERVING WOOD

(76) Inventor: Richard F. Stockel, 475 Rolling Hills Rd., Bridgewater, NJ (US) 08807

( * ) Notice: Subject to any disclaimer, the term of this patent is extended or adjusted under 35 U.S.C. 154(b) by 0 days.

(21) Appl. No.: 10/443,721

(22) Filed: May 23, 2003

(65) Prior Publication Data

US 2004/0234492 A1    Nov. 25, 2004

(51) Int. Cl.
*A01N 3/00* (2006.01)
*B05D 7/06* (2006.01)
*C09D 5/14* (2006.01)
*C09D 5/16* (2006.01)
*C09K 15/16* (2006.01)

(52) U.S. Cl. .............. 427/440; 427/325; 424/78.08; 424/78.01; 424/78.27; 106/18.21; 106/18.24; 252/401; 252/404; 252/602; 252/607

(58) Field of Classification Search .......... 427/325, 427/440; 252/602, 607, 401, 404; 106/18.21, 106/18.24; 424/78.01, 78.27
See application file for complete search history.

(56) References Cited

U.S. PATENT DOCUMENTS

| | | | | |
|---|---|---|---|---|
| 4,648,988 A | * | 3/1987 | Van Dijck et al. | 252/602 |
| 4,666,896 A | * | 5/1987 | Warner et al. | 514/114 |
| 4,980,150 A | * | 12/1990 | Keith | 424/49 |
| 5,575,993 A | * | 11/1996 | Ward et al. | 424/78.1 |
| 5,804,591 A | * | 9/1998 | Valcke et al. | 514/383 |
| 5,985,934 A | * | 11/1999 | Gaffney et al. | 514/672 |
| 5,994,286 A | * | 11/1999 | Desai et al. | 510/386 |
| 6,180,672 B1 | * | 1/2001 | Lichtenberg et al. | 514/561 |
| 6,464,971 B1 | * | 10/2002 | Matthews et al. | 424/78.17 |
| 6,500,466 B1 | * | 12/2002 | Werle et al. | 424/661 |
| 2004/0039353 A1 | * | 2/2004 | Koenig et al. | 604/289 |
| 2004/0234496 A1 | * | 11/2004 | Stockel | 424/78.27 |

FOREIGN PATENT DOCUMENTS

WO    WO 97/25085    * 7/1997

* cited by examiner

*Primary Examiner*—Joseph D. Anthony
(74) *Attorney, Agent, or Firm*—Jack Matalon

(57) ABSTRACT

A method for preserving wood which comprises contacting the wood with a complex of a cationic monomeric or polymeric biocide and an anionic monomeric or polymeric biocide. Insoluble complexes may solubilized in water in the form of an emulsion or microemulsion by adding a nonionic and/or amphoteric surfactant and/or aqueous cosolvent to the complex. Suitable cationic biocides are those that contain functionalities such as amidine, guanidine, biguanide, quaternary, phosphonium, sulfonium and gemini quaternary functionalities. Suitable anionic biocides include: phenolics; saturated, unsaturated or substituted carboxylates; organomercaptide; tetrathiocarbonates; cyanodithioimidocarbamates; dithiodialkylcarbamates; anionic oxides of transition metals; aminocarboxylic acids; aminoorganophosphonic acids; monoalkyl phosphates; dialkylphosphates; and substituted or unsubstituted 2-hydroxy-2,4,6-cycloheptatrianone.

32 Claims, No Drawings

METHOD FOR PRESERVING WOOD

Wood is a natural and renewable resource used extensively in many applications. Unfortunately, if sufficient moisture is present wood can be attached by many organisms, principally brown or white not fungi and insects notably termites. In the U.S. alone damage to residential structures by fungi, and insects is estimated to be in the billions of dollars per year.

Fortunately wood can be treated with biocides to prevent damage caused by fungi or insects. The major wood preservative used today is a water-borne chromated copper arsenate (CCA). About 80% of all treated wood in the U.S. is preserved with CAA. However, there are some major concerns with this treatment such as arsenic exposure, leaching of the metal oxides and the ultimate disposal of the CAA treated wood. Another less used treatment utilizes borate, but thus can only be used in non-leaching applications.

Second generation wood preservatives for residential use are copper-organic mixtures, like ammonia cal copper—quats, and cooper and azoles with and without boron. Cooper has a very serious drawback due to its negative environmental effects, especially in aquatic systems as well as the environmental problem of disposal.

The result of using toxic metals as wood preservatives has lead a worldwide search for a totally organic system, which will largely eliminate the heavy metal toxicity and disposal problems.

Organic biocides are not immune to both economic and toxicity problems. Therefore, developing new all organic biocides require efficacy of protection at low concentration, so that the cost-effectiveness is acceptable by the industry. Low toxicity to humans and mammals is also of prime importance, but yet kill fungi and insects and present no disposal problems.

Fortunately, the wood preservatives of this invention possess all of these desirable properties.

SUMMARY OF THE INVENTION

The present invention is directed to synergistic biocidal compositions containing only organic biocides. The broad-spectrum biocides are synthesized by two procedures. The first involves a metathesis reaction involving the double displacement of a cationic salt of a monomer or polymer biocide with an anionic salt of a monomer or polymer biocide. A second type route involves the reaction of a monomer or polymer free base with a monomer or polymer of an acid biocide. This is known as an acid-base reaction resulting in the formation of a salt of the corresponding acid and base reactants.

According to the present invention, it has been found that these compositions, which are collectively called biocidal complexes, act synergistically to preserve wood.

These combinations of preservatives have been found to have much greater effectiveness than the sum of their individual components. The present invention protects wood against a broad range of insects and fungi. In addition, the present formulations eliminate the need for arsenic, chromium and copper. The latter wood preservatives will be banned by the year 2004, therefore it is imperative that low toxic, effective and environmentally friendly wood preservatives be developed. The present invention's compositions fore fill these criteria.

Another advantage of this invention is the fact that these biocidal complexes can easily be solubilized in a mostly aqueous solution by the proper choice of surfactants to yield either emulsions or microemulsions, depending on the co-solvent, which allows excellent penetration of the wood surpramacro-molecular structure.

The use of water-borne wood preservative solution eliminates toxic and expensive organic solvents, which negates the expense of the solvent and disposal thereof.

Yet another major advantage of these biocidal complexes is that the biocides used in this invention have existing EPA and/or FDA registration for multiply applications including annual and human uses. Some are included in the U.S. Federal GRAS (generally recognized as safe) list. This requirement is highly desirable for future usage.

In addition to metathesis reactions to prepare the compositions of this invention, it is also possible to form some of these compositions by an acid-base reaction. This involves the direct combination of a free base and an organic compound, which has hydrogen which can protonate the free base. This synthetic route is particularly useful, when preparing complexes of the very effective anti-fungal compound known as azoles. Azoles have basic nitrogen atoms available for protonation by organic compounds capable of donating a proton.

DETAILS OF THE INVENTION

This invention relates to new biocidal complexes prepared by metathesis synthesis involving either a monomeric or polymeric cationic biocide reacted with the anionic form of a biocide of a monomeric or polymeric biocide. A second synthetic route is possible, and it involves the reaction of an acid with a base to yield a salt like product. This is feasible when the conjugate base (free base) of the cation is reacted with the conjugate acid of the anion provided the pkb and/or pka are sufficiently either a strong base or strong acid. These complexes tend to have low water solubility therefore for many, but not all applications it is necessary to prepare emulsions or microemulsions to obtain a stable aqueous solution. However to perform as wood preservatives it is necessary to solubilize these compositions. These complexes are very effective biocides against a variety of bacteria, fungi and other microorganisms and insects.

Individually, the biocides of this invention are well known in the published literature, however the complexes of this invention are quite unique, novel and represent new biocidal compositions, emulsion, and microemulsions thereof.

In accordance with this invention, the effectiveness of individual biologically active compounds can be enhanced by the formation of these complexes as described by this invention. Thus the combination of a bioactive cation with a bioactive anion improves the overall biological activity.

This invention has other important safety and toxicity implications because the resulting complex can be composed of either EPA or FDA approved materials.

Another advantage involves the green chemistry used in synthesizing these compositions. Fortunately, the metathesis reaction can be carried out in a totally aqueous medium. The by-product of this reaction is a salt, which does not represent any serious environmental problem for disposal. In fact, many salts can be recycled for other uses. If the acid-base reaction is appropriate, then there is no by-product at all.

While the literature is replete with many patents and articles concerning the individual components of this invention, there is scarce mention of preparing the complexes of this invention. For example, WO 97/25085 describes the combination (admixture) of chlorhexidine with triclosan to contribute antimicrobial activity when applied to medical devices and the like. The inventors do not anticipate our technology, because no mention is made about a chemical reaction between these two biocides, nor does the method they use to apply these biocides allow the formation of a complex.

U.S. Pat. No. 5,575,993 discloses compositions of polyionenes with anionic biological species. However, my invention is not anticipated by 993', since the two are significantly different from each other. These differences are clearly delineated in 993'whereby only part of the polyionene anion is replaced by a bioactive species, from about 0.005 to about 0.33 or 0.50 degree of substitution depending on the specific polyionene used. All of the resulting compositions are very soluble in water, unlike the compositions of my invention, prior to solubilization with the assistance of surfactants and cosolvents.

The invention will be illustrated by the following examples, which, it will be understood, are not intended to be limiting, but merely illustrative.

Chlorhexidine reacted with anionic polymers like algin or or carboxymethylcellulose is taught in U.S. Pat. No. 4,980,150. The purpose of this invention is to prepare a water insoluble salt which has no biocidal synergy, and its' sole purpose is to form a granulated powder to be used as a dentifrice.

Finally there is U.S. Pat. No. 6,500,466, which teaches the preparation of chlorhexidine sugar acids or lactones of sugars. The resulting compositions have exceptional storage stability. No evidence is provided concerning improved biocidal activity.

List of Specific Bioactive Cationic Agents

The following monomeric and polymeric bioactive cationic agents are illustrative of this invention. They by no means represent all possible cationic biocides, but instead are examples of the broad array available to a practitioner who wishes to carry out the scope of this invention.

Examples
Polyhexamethylene biguanide hydrochloride salt
Polyhexamethylene guanidine hydrochloride salt
Dimethyldidecyl ammonium chloride
Benzalkonium chloride
Bemzethonium chloride
Chlorhexidine digluconate
Polyionenes, e.g., Poly(dimethyl butenyl ammonium chloride)alpha, omega-bis (triethanol-ammonium chloride
Propamidine
Dibromopropamidine
Poly(oxyethylene(dimethylimino)ethylene(dimethylimino)ethylene dichloride
Dequalinium chloride
Polyquaternium 2
Hexetidine
Cetyl pyridinium chloride
Tetrakis(hydroxy methyl)phosphonium sulfate
Gemini quats, e.g., -ethanediyl-α,w-bis(dodecyldimethyl) ammonium halide
Quaternary ammonium dendrimeric biocides (U.S. Pat. No. 6,440,405)
Long chain sulfonium salts
Long chain phosphonium salts
Delmopinol
Alexidine It is understood that these cationic antimicrobial agents can be other salts besides the hydrochloride. Some examples are hydroxy carboxylic acids, amino acids, sulfonates, and phosphates to name just a few examples. One skilled in organic chemistry could find other suitable substitutes.

The specific biocides described are illustrative of this invention, but do not represent a complete inventory of all the possible combinations possible. Anyone skilled in the art of chemistry and biology can conceptualize other modifications. In particular, some of the polymeric species useful for carrying out this invention could be further modified by varying the repeating units or by end capping. U.S. Pat. Nos. 4,891,423 and 5,741,886 are examples of further enhancing the antimicrobial activities of phmb. Other such examples for different polymeric systems also exit.

List of Specific Bioactive Anionic Agents

The following monomeric and polymeric bioactive anions represent a partial list of actives, which can be utilized in this invention. Knowledgeable persons familiar with biocides can conjure other possible anionic substitutes. In keeping with the spirit this of this invention, the list below is illustrative as working examples to achieve very broad antimicrobial activity for a variety of applications.

Sodium hydroxymethyl glycinate
Sodium tetrathiocarbonate
Sodium tribromosalicylanilide
Sodium tribromophenol
Sodium 2-bromo-4-hydroxy acetophenone
Disodium cyanodithioimidocarbamate
Potassium N-hydroxymethyl dithiocarbamate
Sodium allyl paraben
Sodium salicylanilide
Disodium bithional
Sodium trichloroacetate
Sodium stearate
Sodium mercaptobenozthiazole
Sodium dithiodimethyl carbamate
Sodium undecylenic acid
Sodium ortho-phenylphenol
Dissodium hexachlorophene
Sodium triclosan
Sodium 2,6-di-t-butyl, 4-methyl phenol
Sodium tetraborate
Sodium polyphosphate
Disodium tetrabromobisphenol-A
Disodium tungstate
Disodium molybdate
Poly anionic compositions like polydivinyl ether-maleic anhydride alternating copolymer
Anionic dendrimers (U.S. Pat. No. 6,464,971)
Chitosan derivatives having carboxylate, sulfate, sulfonate, phosphonate or phosphate anionic functional groups present in the molecule
EDTA and derivatives having carboxylate anions
1-hydroxy ethane-1,1-diphosponic acid
nitrilotris(methylenephosphonic acid)
ethylenediaminetetrakis(methylene-phosphonic acid)
mono or di alkyl phosphates or mixtures thereof
aminophosphonic acids Surfactants Experimentally, it has been determined that the preferred surfactants, which form microemulsions or emulsions with the compositions of this invention, are by and large, either of the amphoteric and non-ionic type, or combinations thereof. Highly charged anionic surfactants have the potential to reduce the overall bioactivity of these complexes by causing some degree of precipitation, thereby lessening its effectiveness.

Surfactants that carry a positive charge in strongly acidic media, carry a negative charge in strongly basic media, and form zwitterionic species at intermediate pH's are amphoteric. The preferred pH range for the stability and effectiveness is from about 5.0 to about 9.0. Under this pH range the amphoteric surfactant is mostly or fully in the zwitter (overall neutral charge) form, thereby negating any dilution of bioactivity of the compositions of this invention.

There are several classes of amphoteric surfactants useful for preparing microemulsions or emulsions for the complexes of this invention. These are:
1. N-alkylamino acids
2. alkyldimethyl betaines
3. alkylamino betaines
4. sulfobetaines
5. imidazolines
6. amino or imino propionates Some of the above amphoteric surfactants have moderate to good antimicrobial activity against certain microorganisms, and hence can be synergistic.

Nonionic surfactants have also been found to be useful to form small particle micelles for these complexes. These can be classified as the following:
1. alcohols
2. alkanolamides
   a. alkanolamides
   b. ethoxylated(propoxylated)amides
3. Amine oxides
4. Esters
   a. ethoxylated(propoxylated)carboxylic acids
   b. ethoxylated(propoxylated)glycerides
   c. glycol esters(and derivatives)
   d. mono(di)glycerides
   e. polyglycerol esters
   f. polyhydric alcohol esters and ethers
   g. sorbitan/sorbital esters
   h. di(tri)esters of phosphoric acid
5. Ethers
   a. ethoxylated(propoxylated)alcohols
   b. ethoxylated(propoxylated)lanolin
   c. ethoxylated(propoxylated)polysiloxanes
   d. ethoxylated-propoxylated block copolymers It has been observed that the choice of a effective surfactant system will differ to some degree for each biocidal complex. The choice will depend on the surfactants hydrophilic-lipophilic balance (HLB) to form a stable small particle micelle in an aqueous or aqueous cosolvent medium solution. Also the combination of two or more amphoteric or a amphoteric-nonionic system or two or more nonionic surfactants can also be utilized to achieve satisfactory results.

It has been found that effective concentrations (based on the weight of the complex) of surfactants are in the range of 0.4 weight percent to about 6.0 weight percent.

Solvents

Since the complexes are mostly slightly soluble (~2 wt. %), or insoluble (<2 wt. %) in water, an appropriate solvent is required to solublize the biocidal composition in order to form an emulsion, or a microemulsion. The latter usually needs a cosolvent.

The choice of a solvent to effectively dissolve the complex is dependent on at least two criteria for the purposes of this invention.

In the concentrate form before dilution with additional water for a specific application, it is highly desirable that the concentration of water is about or greater than 70 weight percent of the total solvents present. It is also preferable to have at least 15 weight percent or greater of actives present in the concentrate.

In order to accomplish these minimum levels of solvents and actives, it is incumbent to choose the proper solvents. This can be done by determining the solubility parameter of the complex.

Experimentally, it has been found that when the complex has considerable ionic character and only slightly soluble in water, than alcohols ($C_1$–$C_4$), glycols, glycol ethers, glycol esters, di, tri and poly hydroxylic solvents can be utilized.

When the complex has a predominance of covalent bonding, then it may be necessary to use aprotic dipolar solvents in part, or in toto. Examples of these types of solvents (not all inclusive) are dimethyl formamide, dimethyl sulfoxide, N-methylpyrrolidone, morpholine N-oxide, or dimethyl-2-piperidone and the like. Other useful solvents found are mono/di/tri phosphates or mixtures thereof.

In certain cases whereby the complex has considerable hydrophobic functionality e.g., stearates it may be necessary to use aromatic solvents like toluene or xylene in part or in toto.

Sometimes, it was found necessary to use combinations of the above solvents to achieve stable emulsions or microemulsions for the biocidal complexes of this invention.

In the final analysis, the total amounts of any of the solvents should be kept to a minimum. About 30 weight percent of the concentrate represents the upper limit. With 15 weight percent or less being preferred. These percentages are based only on the total weight of all the solvents present in the concentrate including water.

A second criteria for the selection of a water-solvent system for these complexes is dependent on the specific application. If the intended use is for human or animal applications then the solvents should have a safe toxicity/low irritation profile.

If the end-use is an industrial application, then the choice of solvents is much broader, but still should be relatively safe.

General Synthesis of Potential Wood Preservative Complexes

Metathesis Procedure

The formation of the candidate molecules can be synthesized by straight forward metathesis reactions carried out in aqueous solutions, or aqueous alcohol mixtures.

These bioactive molecules are produced using the ultimate green chemistry approach. Water is the solvent of choice, by-products are harmless salts and yields are excellent to quantitative.

The appropriate cationic moiety is reacted with the desired anionic moiety in water. The concentration of reactants can vary from 20 to about 60 wt. % of the total solution. The reaction takes place at room temperature, and is generally completed within one hour.

The final product is readily removed by decantation of the solvent and isolation of the solid product and generally can be used as is for certain applications.

Acid-Base Formation of the Complexes

This well known facile reaction can be utilized in some cases by the reaction of a conjugate base (free base) of a biocidal cation with the conjugate acid (protonated) of the biocidal anion. This can be represented by the following example.

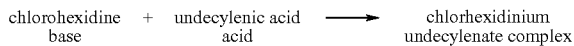

In order for the acid-base process to work the acid component must have a transferable proton (pka) to a basic (pkb) molecule. The reaction is usually conducted in refluxing alcohol (C1–C4), or aqueous alcoholic solutions.

The acid-base reaction is particularly advantageous for the formation of azole fungicides with biocides that have a protonic hydrogen capable to transfer to a base nitrogen in a azole molecule. The family of azoles are either imidazole or triazole derivatives. If the azole can be protonated, then it can be subsequently reacted with a anionic monomer or polymer biocide.

General Method for the Formation of Emulsions/Microemulsions for the Complexes of this Invention The complex is dissolved in the minimum amount of a solvent with the appropriate Hildebrand solubility parameter. The solubility parameter is a numerical value that indicates the relative solvency behavior of a specific solvent. Hildebrand solubility parameters from about 8.5 to about 22.0 are suitable for solubilization of the complexes of this invention.

Depending on the ionic/covalent bonding energies of these compositions, the correct solvent for solubilization will be on the low side, if the bonding has more covalency, and if the bonding is more ionic, then the proper solvent will have a much higher value.

Combinations of solvents are also useful in preparing emulsions or microemulsions.

Next, a amphoteric or non-ionic is added to the dissolved complex. Combinations of the above type surfactants can also be utilized.

The complex-solvent-surfactant is then diluted with water to the active concentration required for the particular application to form an emulsion or microemulsion depending on the micellar size and choice of solvents/cosolvents.

Azole (imidazole and 1,2,4-triazole derivatives) are effective antifungal agents useful as wood preservatives. The mechanism of action for the azoles is inhibition of sterol 14-alpha-demethylase. The inhibition of this enzyme impairs the biosynthesis of ergosterol in the cytoplasmic membrane resulting in inhibition of fungal growth.

Some of the commercially available azoles are presented, however this listing is not all inclusive. Many other possible azole antifungal agents are possible to use for this application.

Examples of benzimidazoles as effective fungicides for the protection of wood against fungi are benomyl, carbendazim, fuberidazole and thiabendazol. Examples of 1,2,4,-triazole azoles compounds having excellent antifungal agents as wood preservatives are bromuconazole, cyproconazole, difenoconazole, diniconazole, epoxiconazole, fenbuconazole, fluguinconazole, flusilazole, hexaconazole, metaconazole, prochloraz, propiconazole, tebuconazole, tetraconazote, triflumizole, flutriafole, myclobutanil, and penconazole.

EXAMPLES

Solubilization of Complexes Concentrates Dilutable with Water 1. phmb triclosante
   15.21 wt. % solids
   20 g active
   100 g methanol
   10 g NMP
   1.5 g Tego Betaine Z (real)
2. chlorhexidinium di (diethyldithiocarbamate)
   13.82 wt. % solids
   15 g active
   75 g ethanol
   15 g DMF
   3.5 g Tween 20 (real)
3. benzalkonium diethbyldithiocarbamate
   18.43 wt. % solids
   20 g active
   80 g isopropanol
   5 g DMSO
   3.0 g Tween 20 (real)
4. chlorhexidinium di (2-mercaptobenzothiazole)
   17.74 wt. % solid
   20 g active
   90 g NMP
   2.75 g Tego Betaine Z (real)
5. didecyldimethyl ammonium 2-mercapto-benzothiazole
   19.41 wt. % solids
   20 g active
   65 g isopropanol
   15 g DMF
   3.0 g Tego Betaine (real)
6. chlorhexidinium di(2-mercapto-pyridine N-oxides)
   22.22 wt. % solids
   20 g active
   60 g DMF
   10 g N-octyl NMP
7. phmb 2-mercapto-pyridine N-oxide
   28.41 wt. % solids
   25 g active
   50 g NMP
   10 g isopropanol
   3 g phospholipid CDM (real)
8. Tetrakis (hydroxymethyl phosphonium 2-mercapto-pyridine N-oxide
   23.04 wt. % solids
   25 g active
   70 g isopropanol
   10 g DMSO
   3.5 g Tego Betaine Z (real)
9. Poly (oxyethylene (dimethyliminio) ethylene (dimethyl iminio) ethylene di(2-mercapto-pyridine N-oxide
   21.51 wt. % solids
   20 g active
   60 g isopropanol
   10 g NMP
   3.0 g Tego Betaine Z
10. chlorhexidinium di (triclosante)
    20.20 wt. % solids
    20 g active
    70 g ethanol
    5 g DMF
    2 g each Tween 20/Tego Betaine Z (real)
11. chlorhexidinium di (stearate)
    16.39 wt. % solid
    20 g
    25 g isopropanol
    75 g NMP
    2 g each of Tween 20 and Tego Betaine Z (real)
12. di phmb ethylenediaminetetraacetic acid (diacetate)
    20 g
    30 g DMSO
    70 g isopropanol
    3.5 g Tego Betaine Z (real)

Microbiological Tests

The bacteriostatic activity of several complexes was investigated by testing at 0.1 wt. % using Oxoid No. 2 nutrient broth and inoculating the broth with 1 ml of a 24 hour broth culture of the test organisms. After incubation at the optimum growth temperature of the organism for 48 hours.

The organisms tested were:
*Staphylococcus aureous* (gram positive)
*Pseudomonas aeruginosa* (gram negative)
*Escherichia coli* (gram negative)

Compounds 1, 5, 6, 7, 8, 9 and 10 were tested and found to be bacteriostatic at 0.1 wt. % against the above 3 organisms. These complexes were the only one studied using this test.

Experimental Results

The following five wood preservatives were prepared for testing according to ASTM Stanard D 1413.
1. chlorhexidine (CH)—Omadine[a] 1:2 complex
2. Polyhexamethylene biguanide—Omadine 1:1 complex
3. Bardac[b] 2250—Omadine 1:1 complex
4. Tetrakis(hydroxylmethyl)phosphonium 0 Omadine 1:1 complex
5. B-55[c] polyionene—Omadine 1:2 complex
   a) Omadine is 2-mercapto pyridine N-oxide
   b) Barclac 2250 is dodecyldimethyl ammonium chloride
   c) B-77 is poly(oxyethylene(dimethyliminio)ethylene (dimethylimino)ethylene dichloride Biological Evaluation The ASTM 1413 standard soil block test was performed (ASTM 1999) Five soil bottles of each treatment and solution concentration (plus untreated controls) were exposed to the brown-rot fungus *Gloeophyllum trabeum* for 12 weeks. Two soil bottles with no fungus were also run to monitor any leaching of chemicals. Specimens were removed from test after 12 weeks exposure and conditioned until constant weight in the conditioning room (27° C./30°RH). The extent of decay was determined by weight loss.

Results

Table 1 shows the WPG's (Weight percent again) and standard deviations after treatment. The anion in all cases was omadine.

TABLE 1

Percentage Weight Gain after Chemical Treatment

| | Unleached | |
|---|---|---|
| | WPG (%) | STDEV |
| CH 1% | 4.050 | 0.152 |
| PHMB 1% | 2.582 | 0.165 |
| BARDAC 1% | 1.906 | 0.103 |
| THP 1% | 1.165 | 0.091 |
| B-77 1% | 1.165 | 0.091 |
| Untreated Control | 0.181 | 0.046 |

Table 2 shows the weight losses and standard deviations, after the 12-week soil block test with *G. trabeum*. In the soil block test with solid wood a weight loss of 5% or lower is considered a success, and the untreated controls should be about 50% weight loss. In this study the controls show 44% (+/−11%) for unleached speciumens.

TABLE 2

Weight losses and Standard Deviations after 12-week soil block test with the brown-rot fungus *G. trabeum*. Unleached

| | Fungus | | No Fungus | |
|---|---|---|---|---|
| | Wt. Loss % | STDEV | Wt. Loss % | STDEV |
| CH 1% | 1.57 | 0.22 | 1.14 | 0.01 |
| PHMB 1% | 0.52 | 0.18 | 2.46 | 3.66 |
| BARDAC 1% | 0.21 | 0.05 | 0.09 | 0.00 |

TABLE 2-continued

Weight losses and Standard Deviations after 12-week soil block test with the brown-rot fungus *G. trabeum*. Unleached

| | Fungus | | No Fungus | |
|---|---|---|---|---|
| | Wt. Loss % | STDEV | Wt. Loss % | STDEV |
| THP 1% | −0.07 | 0.04 | −0.30 | 0.05 |
| B-77 1% | 0.31 | 0.06 | −0.07 | 0.01 |
| Untreated Control | 44.21 | 11.06 | −0.18 | 0.00 |

All of the chemical treatments performed very well and show promising wood preservation properties.

Table 3 lists a series of Polyhexamethylene biguanide derivatives whereby the polymeric biocide has been modified with different anions, endcapping or by changing the backbone.

TABLE 3

| | G. trabeum (1 wt. %) | | T. versicolor (1 wt. %) | |
|---|---|---|---|---|
| Composition | Avg. | Std. | Avg. | Std. |
| phmb tetraborate | 1.0 | 0.2 | 1.2 | 0.3 |
| phmb N,N-dimethyl dithio-carbamate | 2.2 | 0.3 | 1.9 | 0.4 |
| phmb triclosan | 0.3 | 0.3 | 1.5 | 0.2 |
| phmb end-capped with 2,4-dichlorobenzyl amino-mercapto-benzothiazole | 3.0 | 0.5 | 2.2 | 0.5 |
| polybiguanide prepared from biscyanohexamethylene and 2,2'.diamino-4-4'-bigthiazole-triclosan | 2.7 | 1.6 | 2.3 | 0.6 |

The invention claimed is:

1. A method for preserving wood which comprises contacting the wood with a wood preserving amount of a complex of a cationic biocide and an anionic biocide, wherein said cationic biocide contains a functionality selected from the group consisting of amidines, azoles, guanidines, biguanides, phosphoniums and sulfoniums, and wherein said anionic biocide contains a functionality selected from the group consisting of phenolics, saturated carboxylates, unsaturated carboxylates, substituted carboxylate, organomercaptides, tetrathiocarbonates, cyanodithio-imidocarbamates, dithiodialkylcarbamates, anionic oxides of transition metals, aminocarboxylic acids, amninoorgano-phosphonic acids, monoalkylphosphates, dialkylphosphates, and substituted or unsubstituted 2-hydroxy-2,4,6-cyoloheptatrianone.

2. The method of claim 1 wherein the complex is present in the form of an aqueous emulsion.

3. The method of claim 1 wherein the complex is present in the form of an aqueous microemulsion.

4. The method of claim 1 wherein the complex further comprises at least one nonionic and/or amphoteric surfactant and/or aqueous cosolvent.

5. The method of claim 4 wherein the amphoteric surfactant comprises Tego Betaine.

6. The method of claim 1 wherein the cationic biocide comprises a chlorhexidine salt.

7. The method of claim 1 wherein the cationic biocide comprises a dibromopropamidine salt.

8. The method of claim 1 wherein the cationic biocide comprises a tetrakis(hydroxymethyl)phosphonium salt.

9. The method of claim 1 wherein the cationic biocide comprises a salt selected from the group consisting of a polyhexamethylene guanidine salt, a polyhexamethylene biguanide salt, a mono-end-capped modified polyhexamethylene guanidine salt, a mono-end-capped modified polyhexamethylene biguanide salt, a di-end-capped modified polyhexamethylene guanidine salt and a di-end-capped polyhexamethylene biguanide salt.

10. The method of claim 1 wherein the cationic biocide comprises a poly(oxyethylene-(dimethylimino)ethylene (dimethylimino)ethylene salt.

11. The method of claim 1 wherein the cationic biocide comprises hexetidine.

12. The method of claim 1 wherein the cationic biocide comprises alexidine.

13. The method of claim 1 wherein the anionic biocide comprises triclosan.

14. The method of claim 1 wherein the anionic biocide comprises dodecyl gallate.

15. The method of claim 1 wherein the anionic biocide comprises ortho-phenyl phenol.

16. The method of claim 1 wherein the anionic biocide comprises 2-mercapto-pyridine-N-oxide.

17. The method of claim 1 wherein the anionic biocide comprises tetrabromobisphenol A.

18. The method of claim 1 wherein the anionic biocide comprises dithiodimethyl carbamate.

19. The method of claim 1 wherein the anionic biocide comprises 2-mercapto-benzothiazole.

20. The method of claim 1 wherein the anionic biocide comprises hinikitiol.

21. A method for preserving wood which comprises contacting the wood with a wood preserving amount of a complex of a cationic monomeric biocide and an anionic biocide, wherein said anionic biocide contains a functionality selected from the group consisting of phenolics, saturated carboxylates, unsaturated carboxylates, substituted carboxylates, organomercaptides, tetrathiocarbonates, cyanodithioimidocarbamates, dithiodialkylcarbamates, anionic oxides of transition metals, aminocarboxylic acids, aminoorganophosphonic acids, monoalkylphosphates, dialkylphosphates, and substituted or unsubstituted 2-bydroxy-2,4,6-cycloheptatrianone.

22. The method of claim 21 wherein the monomeric cationic biocide contains a quaternary or gemini quaternary functionality.

23. The method of claim 21 wherein the cationic biocide comprises a dodecyldimethyl ammonium salt.

24. The method of claim 21 wherein the cationic biocide comprises a poly[dimethylbutenyl-ammonium-α,o-bis(triethanolammonium)]salt.

25. The method of claim 21 wherein the monomeric cationic biocide comprises dimethyl didecyl ammonium chloride.

26. The method of claim 21 wherein the monomeric cationic biocide comprises benzalkonium chloride.

27. The method of claim 21 wherein the monomeric cationic biocide comprises benzethonium chloride.

28. The method of claim 21 wherein the monomeric cationic biocide comprises dequalinium chloride.

29. The method of claim 21 wherein the monomeric cationic biocide comprises a quaternary ammonium dendrimer.

30. The method of claim 21 wherein the monomeric cationic biocide comprises an ethanediyl-α,w-bis(dodecyldimethyl)ammonium halide.

31. A method for preserving wood which comprises contacting the wood with a wood preserving amount of a complex of a cationic biocide and an anionic biocide, wherein said anionic biocide contains a functionality selected from the group consisting of organomercaptides, tetrathiocarbonates, cyanodithioimidocarbamates, dithiadialkylcarbamates, anionic oxides of transition metals, aminoorganophosphonic acids, monoalkylphosphates, dialkylphosphates, and substituted or unsubstituted 2-hydroxy-2,4,6-cycloheptatrianone.

32. The method of claim 31 wherein the cationic biocide comprises polyquaternium 2.

* * * * *